(12) United States Patent
Rougeot et al.

(10) Patent No.: US 7,423,020 B2
(45) Date of Patent: *Sep. 9, 2008

(54) TREATMENT OF MOOD DISORDERS BY ADMINISTRATION OF SMR1

(75) Inventors: Catherine Rougeot, Chevreuse (FR); Francois Rougeon, Sevres (FR)

(73) Assignees: Institut Pasteur, Paris (FR); Centre National de la Recherche Scientifique (C.N.R.S), Paris (FR)

( * ) Notice: Subject to any disclaimer, the term of this patent is extended or adjusted under 35 U.S.C. 154(b) by 120 days.

This patent is subject to a terminal disclaimer.

(21) Appl. No.: 10/451,073

(22) PCT Filed: Dec. 24, 2001

(86) PCT No.: PCT/IB01/02818

§ 371 (c)(1),
(2), (4) Date: Dec. 30, 2003

(87) PCT Pub. No.: WO02/051434

PCT Pub. Date: Jul. 4, 2002

(65) Prior Publication Data

US 2004/0092486 A1      May 13, 2004

(30) Foreign Application Priority Data

Dec. 24, 2001 (EP) ................................. 00403670

(51) Int. Cl.
*A61K 38/00* (2006.01)
*A61K 38/05* (2006.01)
*A61K 38/12* (2006.01)
*A01N 37/18* (2006.01)

(52) U.S. Cl. ............................... 514/17; 514/2; 514/16; 514/12; 530/300; 530/330; 530/317; 530/323

(58) Field of Classification Search ....................... None
See application file for complete search history.

(56) References Cited

FOREIGN PATENT DOCUMENTS

| FR | WO 90/03981 | * | 4/1990 |
|---|---|---|---|
| WO | 90 03981 | | 4/1990 |
| WO | 98 37100 | | 9/1998 |
| WO | 01 00221 | | 1/2001 |

OTHER PUBLICATIONS

DSM-IV, Fourth Edition. 1994, American Psychiatric Association, Washington, DC. Table of Contents, tree pages including cover.*
Roques, TiPS, 2000, vol. 21, pp. 475-483.*
U.S. Appl. No. 11/594,105, filed Nov. 8, 2006, Rougeot, et al.
U.S. Appl. No. 10/451,073, filed Dec. 30, 2003, US2004/0092486 Rougeot, et al.

* cited by examiner

*Primary Examiner*—Olga N Chernyshev
(74) *Attorney, Agent, or Firm*—Oblon, Spivak, McClelland, Maier & Neustadt, P.C.

(57) ABSTRACT

This invention relates to the use of an agent that modulates the interaction between a SMR1 peptide and a metal-lopeptidase for the preparation of a medicament for preventing or treating a Central Nervous System disorder giving rise to a mental disorder.

5 Claims, 7 Drawing Sheets

SEQUENCE LISTING

<160> NUMBER OF SEQ ID NOS: 12

<210> SEQ ID NO 1
<211> LENGTH: 5
<212> TYPE: PRT
<213> ORGANISM: Rattus norvegicus

<400> SEQUENCE: 1

Gln His Asn Pro Arg
1               5

<210> SEQ ID NO 2
<211> LENGTH: 6
<212> TYPE: PRT
<213> ORGANISM: Rattus norvegicus

<400> SEQUENCE: 2

Arg Gln His Asn Pro Arg
1               5

<210> SEQ ID NO 3
<211> LENGTH: 11
<212> TYPE: PRT
<213> ORGANISM: Rattus norvegicus

<400> SEQUENCE: 3

Val Arg Gly Pro Arg Arg Gln His Asn Pro Arg
1               5                   10

<210> SEQ ID NO 4
<211> LENGTH: 5
<212> TYPE: PRT
<213> ORGANISM: Rattus rattus

<400> SEQUENCE: 4

Gln His Asn Leu Arg
1               5

<210> SEQ ID NO 5
<211> LENGTH: 6
<212> TYPE: PRT
<213> ORGANISM: Rattus rattus

<400> SEQUENCE: 5

Arg Gln His Asn Leu Arg
1               5

<210> SEQ ID NO 6
<211> LENGTH: 6
<212> TYPE: PRT
<213> ORGANISM: Mus sp.

<400> SEQUENCE: 6

Gly Gln His Gly Pro Arg
1               5

<210> SEQ ID NO 7
<211> LENGTH: 6
<212> TYPE: PRT
<213> ORGANISM: Mus sp.

<400> SEQUENCE: 7

Gly Gln His Asp Pro Thr

-continued

```
<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MISC_FEATURE
<222> LOCATION: (1)..(6)
<223> OTHER INFORMATION: This region may encompass VRGPRR, VRGPR, VRGP,
      VRG, VR, V or may not be presented; see specification as filed for
      detailed description of preferred embodiments

<400> SEQUENCE: 8

Xaa Xaa Xaa Xaa Xaa Xaa Gln His Asn Pro Arg
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide motif
<220> FEATURE:
<221> NAME/KEY: MISC_FEATURE
<222> LOCATION: (1)..(6)
<223> OTHER INFORMATION: this region may encompass VRGPRR, VRGPR, VRGP,
      VRG, VR, V or may not be present; see specification as filed for
      detailed description of preferred embodiments
<220> FEATURE:
<221> NAME/KEY: MISC_FEATURE
<222> LOCATION: (9)..(9)
<223> OTHER INFORMATION: Xaa at position 9 (X4) is N, G, or D
<220> FEATURE:
<221> NAME/KEY: MISC_FEATURE
<222> LOCATION: (10)..(10)
<223> OTHER INFORMATION: Xaa at position 10 (X3) is P or L
<220> FEATURE:
<221> NAME/KEY: MISC_FEATURE
<222> LOCATION: (11)..(11)
<223> OTHER INFORMATION: Xaa at position 11 (X4) is R or T

<400> SEQUENCE: 9

Xaa Xaa Xaa Xaa Xaa Xaa Gln His Xaa Xaa Xaa
1               5                   10

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 10

Gly Pro Arg Arg
1

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 11
```

-continued

```
Arg Gly Pro Arg Arg
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide motif

<400> SEQUENCE: 12

Val Arg Gly Pro Arg Arg
1               5
```

TREATMENT OF MOOD DISORDERS BY ADMINISTRATION OF SMR1

The invention relates to the prevention or treatment of Central Nervous System disorders giving rise to mental disorders such as impaired interpersonal and behavioral disorders, which method comprises modulating the interaction of a SMR1 peptide with a metallopeptidase.

The inventors have previously characterized a new rat submandibular gland protein, named SMR1 (submandibular rat 1 protein), which has the structure of a prohormone and whose synthesis is under androgen control (Rosinsky-Chupin et al., (1988), *Proc. Natl. Acad.* Sci. USA; 85(22): 8553-7) and PCT Patent Application No. WO 90/03981). The gene encoding SMR1 belongs to a new multigene family, the VCS family, which has been localized to rat chromosome 14, bands p 21-p 22 (Courty et al., (1996) *Mol. Biol. Evol.* 13(6): 758-66; Rosinsky-Chupin et al., (1995) *Mamm. Genome* 6(2): 153-4)) and for which some human gene members are characterized (Isemura et al, 1997, *J. Biochem* 121: 1025-1030; Isemura et al, 1994, J. Biochem 115: 1101-1106; Isemura et al, 1979, J. Biochem 86: 79-86; Dickinson et al, 1996, Curr Eye Res, 15: 377-386). The gene has an organization similar to a number of hormone precursor genes (Rosinsky-Chupin et al., (1990) *DNA Cell. Biol.* 9(8): 553-9). SMR1 mRNA is expressed in a highly tissue-, age- and sex-specific manner in the acinar cells of the male rat submaxillary gland (SMG) and in the prostate (Rosinsky-Chupin et al., (1993) *Histochem. Cytochem.* 41(11): 1645-9)).

It has been described that, in vivo, SMR1 is selectively processed at pairs of basic amino acid sites in a tissue- and sex-specific manner to give rise to mature peptide products, in a manner similar to the maturation pathway of peptide-hormone precursors (Rougeot et al., (1994) *Eur. J. Biochem.* 219(3): 765-73). The structurally related peptides generated from SMR1 by cleavage at pairs of arginine residues (e.g. the undecapeptide: VRGPRRQHNPR (SEQ ID NO: 3); the hexapeptide: RQHNPR (SEQ ID NO: 2); and the pentapeptide: QINPR (SEQ ID NO: 1)) are in vivo selectively matured from the precursor after processing at pairs of basic amino acid residues by a paired basic aminoacid-converting enzyme, likely the Furine convertase,—differentially accumulated in a tissue-, age- and sex-related manner, and—locally as well as systemically released upon multifactorial neuroendocrine control (Rougeot et al, 1994).

In such a context, the final mature peptide generated from SMR1, named SMR1-Pentapeptide (SMR1-QHNPR) (SEQ ID NO: 1), also named sialorphin, is synthesized predominantly in response to androgen steroids and is constitutively released into the bloodstream in basal condition and acutely released in response to environmental stress, depending on the state of activation of adrenoreceptors controlling the secretory responsiveness of the SMG.

In turn, the circulating SMR1-Pentapeptide is in vivo rapidly and selectively taken up by peripheral targets through specific binding sites, predominantly within renal, bone and dental tissues.

The fact that the target sites of the peptide are mainly localized within the major tissues of ion capture, transport and regulation, gives evidence that SMR1-Pentapeptide might play a local and systemic role in modulating mineral ion homeostasic process, in vivo. Furthermore, associated with the fact that the androgen-regulated SMR1-Pentapeptide is upon environmental stress acutely secreted, these findings led the inventors to postulate that this SMG-specific signaling peptide might participate in mediating integrative reestablishment of dynamic homeostatic responses: to stressful situations within male rat-specific behavioral characteristics such as aggression and/or sexual intercourses, and in relation to female-specific physiological characteristics such as pregnancy and lactation.

WO 98/37 100 discloses that the maturation products of the SMR1 protein, specifically the peptide of structural formula XQHNPR (SEO ID NO: 8), recognize specific target sites in organs that are deeply involved in the mineral ion concentration. This discovery has led the inventors to assign to the SMR1-peptide (especially the SMR1-pentapeptide, hexapeptide or undecapeptide) an active role in the regulation of the metal ion concentrations in the body fluids and tissues, and thus a therapeutic role of these peptides in all the metabolic disorders related to a mineral ion imbalance.

Namely, the therapeutic peptides disclosed therein are useful for treating or preventing bone, teeth, kidney, intestine, pancreas, stomach, or salivary gland disorders caused by a mineral ion imbalance in the body fluids or tissues, namely hyper- or hypo-parathyroidism, osteoporosis, pancreatitis, submandibular gland lithiasis, nephrolithiasis or osteodystrophy.

On the basis of the hypothesis mentioned above, a behavioral pharmacological approach has been undertaken. SMR1-peptide, especially SMR1-Pentapeptide was found to induce a dose-dependent improvement on the sexual behavior of adult male rats with a loss of the aggressive impulse behavior seen in control rats (PCT patent application WO 01/00 221).

To elucidate the pathways that have taken place in the SMR1-peptide action, one of the essential steps was to investigate the molecular characteristics of the peptide-receptor sites. The isolation of the membrane binding site accessible to the systemic administration or radiolabelled SMR1-Pentapeptide, especially within the renal outer medulla has been achieved. The identification of its amino-acid sequence has revealed that the cell surface molecule which binds the peptide in vivo, is a membrane metallopeptidase and more specifically a mammalian type II integral membrane zinc-containing endopeptidase, i.e. Neutral EndoPeptidase 24-11 or NEP, also named Enkephalinase that belongs to the Neprilysin subfamily, which plays critical role in the functional potency of various peptidergic signals. Moreover, the in vivo direct interaction of rat kidney NEP and SMR1-Pentapeptide was demonstrated in vitro using purified rabbit kidney NEP.

Furthermore, at the level of whole rat body a good (topological and kinetical) correspondence was found in vivo between the distribution of target organs accessible to circulating radiolabelled SMR1-Pentapeptide and that of known synthetic NEP inhibitor (3HHACBO-Gly) (Sales et al, (1991) *Regulatory Peptides* 33, 209-22). Otherwise, a number of observations argues for the hypothesis that SMR1-peptide is a SMG-derived natural modulator, especially an inhibitor, of the NEP activity:

1—the SMR1-Pentapeptide tissue uptake was found to be pharmacokinetically and biochemically stable in vivo, 2—the SMR1-peptide does not share the residues required to be a NEP substrate, seeing that the NEP preferentially cleaves peptides between the X-Phe bond, and 3—the SMR1-Pentapeptide has strong zinc-chelating group, which has been designed for the potent synthetic NEP inhibitors.

In view of the numerous physiological NEP substrates (namely the peptide hormones: Enkephalins, Substance P, Bradykinin, Angiotensin II and atrial natriuretic peptide), physiological consequences of the NEP/SRM1-peptide interaction are expected to impact on the control of central and peripheral pain perception, inflammatory phenomena, arterial tone and/or mineral exchange (Roques et al, 1993).

Neutral endopeptidase, NEP 24-11, is distributed both in nervous and peripheral tissues of mammals, and in the periphery it is particularly abundant in the kidney and placenta. In these tissues the cell-surface metallopeptidase NEP participates in the postsecretory processing and metabolism of neuropeptides, systemic immunoregulatory peptides and peptide-hormones. By controlling the active levels of circulating or secreted regulatory peptides, NEP modulates their physiological receptor-mediated action. Hence, the membrane-anchored NEP is involved in regulating the activity of: potent vasoactive peptides such as Substance P, Bradykinin (BK), Atrial Natriuretic peptide (ANP), and Angiotensin II (AII); potent inflammatory/immunoregulatory peptides such as Substance P and BK and flet-Leu-Phe (fMLP); potent opioid neuropeptides such as Met and Leu-Enkephalins (Enk) and potent mineral exchange and fluid homeostasis regulatory peptides such as ANP, C-type Natriuretic Peptide (CNP) and B-type Natriuretic Peptide (BNP). However the levels of these peptides are changed through the NEP-induced formation/degradation only in regions where they are tonically released or where their release is triggered by a stimulus.

From an integrative point of view, the NEP biological activity is to control the active levels of peptidergic signals involved in arterial tension regulation, in inflammatory phenomena and in water-mineral homeostasis, as well as, in the control of pain processing. From a clinical point of view, this substantiates the fact that NEP is an important drug target in various disease states. For example, by inhibiting NEP, thereby increasing the levels and duration of action of central or peripheral endogenous opioids, an analgesic or antidiarrheal agent could be obtained, or by inhibiting endogenous AII formation and substance P, BK and ANP inactivation, antihypertensive, natriuretic and diuretic agents could be obtained. The main advantage of modifying the concentrations of endogenous peptides by use of NEP inhibitors is that the pharmacological effects are induced only at receptor stimulated by the natural effectors, and are critically dependent on the tonic or stimulus-evoked release of the natural effectors happening upon environmental, behavioral and physiopathological stressful situations (Roques et al, (1993) *Pharmacological Reviews* 45, 87-146). It is important to stress that in such stressful context, the natural potential NEP-modulator, SMR1-peptide, will be also acutely and tonically released, distributed and taken up by its systemic target tissues, especially by the renal NEP sites (Rougeot et al, 1997). Thereby, the SMR1-peptide would be in vivo kinetically bioavailable to modulate NEP activity and so to optimize the local and systemic inflammatory, pressor and/or ion homeostatic responses to stress. The integrative point of view is in concordance with the assumption that circulating Submaxillary Gland (SMG)-derived factors might participate in integrative reestablishment of homeostatic responses to physiological or pathological "stress states" (injury, trauma or infection), rather than contribute to the resting homeostatic steady state (Rougeot et al, (2000) *Peptides* 21, 443-55).

From a general point of view, evidence of a physiological significance demonstrates the existence of a Cervical Sympathetic Trunk (CST)-SMG neuroendocrine axis that plays an integral role in physiological adaptations and contributes to the maintenance of homeostasis in mammals, especially under the "stress conditions" seen in rodents with tissue damage, inflammation, and aggressive behavior. The data gathered in the laboratory provide convincing evidence that SMR1-peptide is a novel signaling mediator, adapted to the sex, and species-specific environmental, behavioral and physiological characteristics, tonically and dynamically mobilized upon urgent situations, in the way to optimize both local and systemic nociceptive, inflammatory, pressor and/or ion homeostatic responses, through regulation of the membrane-bound NEP activity. Otherwise, the SMR1-peptide, which is to date the first natural regulator of the peripheral NEP activity identified, seems to be designed as a new class of therapeutic molecules as this metallopeptidase is well-conserved especially between rat, rabbit and human species with sequence homology ≧90% (Genbank access number P08473, Malfroy et al, FEBS Lett, 1988, 229(1), 206-210,); Genbank access number NP 258428, Bonvouloir et al, DNA Cell Biol, 2001, 20(8), 493-498; Genbank access number NP 036740, Malfroy et al, Biochem Biophys Res. Commun, 1987, 144, 59-66).

The evidence provided by the inventors together with the striking homology with the NEP sequences between species further show that the SMR1-peptide acts as natural modulator/inhibitor of membrane metallopeptidases, notably zinc metallopeptidases.

A subject of the present invention is thus a method for preventing or treating a Central Nervous System disorder giving rise to a mental disorder, which method comprises modulating the interaction of a SMR1 peptide with a metallopeptidase.

Another subject of the invention is the use of an agent that modulates the interaction between a SMR1 peptide and a metallopeptidase for the preparation of a medicament for preventing or treating a Central Nervous System disorder giving rise to a mental disorder.

Metallopeptidases

Examples of mammalian membrane metallopeptidases besides NEP are ECE (Endothelin-Converting Enzymes), in particular ECE1 and ECE2, the erythrocyte cell-surface antigen KELL and the product of PEX gene associated with X-linked hypophosphatemic rickets, as well as ACE (Angiotensin Converting Enzyme).

Natural NEP substrates are mainly the peptide hormones: Enkephalins, Substance P, Bradykinin, Angiotensin II and Atrial Natriuretic Peptide which play key role in the control of central and peripheral pain perception, inflammatory phenomena and/or arterial tone.

Modulating Agents

By "modulating agent", it is understood that the agent has the capacity either to increase or decrease the metallopeptidase activity or to prevent the normal interaction between the endogenous SMR1-peptide and said metallopeptidase.

"Endogenous" refers to a molecule (herein a SMR1-peptide) that is naturally expressed or matured in tissues of a patient to be treated.

According to the present invention, agents that modulate the interaction of SMR1-peptide with a metallopeptidase can be identified by screening methods, and/or designed, e.g. taking into account the structure of the endogenous SMR1 protein and peptides.

For the purpose of designing modulating agents, one may consider the structure of the SMR1 protein, a peptide generated from SMR1, also called a maturation product of the SMR1 protein, or one of the biologically active derivatives of said protein or said maturation product.

One may further consider compounds of structural formula (1):

         (SEQ ID NO: 9)

wherein $X_1$ denotes a hydrogen atom or $X_1$ represents an amino acid chain selected from the following: $X_1$=R or G, $X_1$=RR, or $X_1$=PRR, or $X_1$=GPRR (SEQ ID NO: 10), or $X_1$=RGPRR (SEQ ID NO: 11), or $X_1$=VRGPRR (SEQ ID NO: 12), $X_2$ denotes N, G or D, $X_3$ denotes P or L and $X_4$ denotes R or T.

Preferred peptides comprise peptides of sequence QHNPR (SEQ ID NO: 1), RQHNPR (SEQ ID NO: 2) and
  VRGPRRQHNPR (SEQ ID NO: 3) from Ratus norvegius,
QHNLR (SEQ ID NO: 4) and RQHNLR (SEQ ID NO: 5) from Ratus ratus,
  GQHGPR (SEQ ID NO: 6) and GQHDPT (SEQ ID NO: 7) from mouse.

In the above aminoacid sequences:
  Q represents Glutamine,
  H represents Histidine,
  N represents Asparagine,
  G represents Glycine,
  P represents Proline,
  R represents Arginine,
  L represents Leucine,
  T represents Threonine,
  D represents Aspartic acid, and
  V represents valine.

The agents that can modulate the interaction between an endogenous SMR1-peptide and a metallopeptidase include peptides, or other organic molecules. It may be a compound or a mixture of compounds, such a natural extract. The structure of this modulating agent may be characterized or still unknown, so long as the agent shows an ability to modulate the interaction of a SMR1-peptide with a metallopeptidase.

For purposes of the invention, a "peptide" is a molecule comprised of a linear array of amino acid residues connected to each other in the linear array by peptide bonds. Such linear array may optionally be cyclic, i.e., the ends of the linear peptide or the side chains of amino acids within the peptide may be joined, e.g., by a chemical bond. Such peptides according to the invention may include from about three to about 500 amino acids, and may further include secondary, tertiary or quaternary structures, as well as intermolecular associations with other peptides or other non-peptide molecules. Such intermolecular associations may be through, without limitation, covalent bonding (e.g., through disulfide linkages), or through chelation, electrostatic interactions, hydrophobic interactions, hydrogen bonding, ion-dipole interactions, dipole-dipole interactions, or any combination of the above.

Peptides according to the invention can be conveniently synthesized using art recognized techniques (see e.g., Merrifield, J. Am. Chem. Soc. 85: 2149-2154).

Peptidomimetics are also compounds of interest.

Preferred peptidomimetics retain the binding specificity and/or physiological activity of the parent peptide, as described above. As used herein, a "peptidomimetic" is an organic molecule that mimics some properties of peptides, preferably their binding specificity and/or physiological activity. Preferred peptidomimetics are obtained by structural modification of peptides according to the invention, preferably using unnatural amino acids, D aminoacid instead of L aminoacid, conformational restraints, isosteric replacement, cyclization, or other modifications. Other preferred modifications include without limitation, those in which one or more amide bond is replaced by a non-amide bond, and/or one or more amino acid side chain is replaced by a different chemical moiety, or one of more of the N-terminus, the C-terminus or one or more side chain is protected by a protecting group, and/or double bonds and/or cyclization and/or stereospecificity is introduced into the amino acid chain to increase rigidity and/or binding affinity.

Still other preferred modifications include those intented to enhance resistance to enzymatic degradation, improvement in the bioavailability in particular by nervous and gonad tissues and more generally in the pharmacokinetic properties and especially comprise:
  protecting the $NH_2$ and COOH hydrophilic groups by esterification (COOH) with lipophilic alcohols or by amidation (COOH) and/or by acetylation ($NH_2$) or added carboxyalkyl or aromatic hydrophobic chain at the $NH_2$ terminus;
  retroinversion or reduction isomers of the CO—NH amide bonds or methylation (or ketomethylene, methyleneoxy, hydroxyethylene) of the amide functions;
  substitution of L aminoacids for D aminoacids;
  dimerization of amino acid peptide chain.

All of these variations are well known in the art. Thus, given a peptide sequence, those skilled in the art are enabled to design and produce peptidomimetics having binding characteristics similar to or superior to such peptides (see e.g., Horwell et al., Bioorg. Med. Chem. 4: 1573 (1996); Liskamp et al., Recl. Trav. Chim. Pays-Bas 1: 113 (1994); Gante et al., Angew. Chem. Int. Ed. Engl. 33: 1699 (1994); Seebach et al., Helv. Chim. Acta 79: 913 (1996)).

The peptides used according to the present invention may be prepared in a conventional manner by peptide synthesis in liquid or solid phase by successive couplings of the different amino acid residues to be incorporated (from the N-terminal end to the C-terminal end in liquid phase, or from the C-terminal end to the N-terminal end in solid phase) wherein the N-terminal ends and the reactive side chains are previously blocked by conventional groups.

For solid phase synthesis the technique described by Merrifield may be used in particular. Alternatively, the technique described by Houbenweyl in 1974 may also be used.

For more details, reference may be made to WO 98/37 100.

The peptides used in the therapeutic method according to the present invention may also be obtained using genetic engineering methods. The nucleic acid sequence of the cDNA encoding the complete 146 amino acid SMR1 protein has been described in the PCT Patent Application No. WO 90/03891 (Rougeon et al.) For the biologically active peptide derivatives of the SMR1-peptide, for example a derivative of $X_1QHX_2X_3X_4$, (SEQ ID NO: 9) a person skilled in the art will refer to the general literature to determine which appropriate codons may be used to synthesize the desired peptide.

The methods that allow a person skilled in the art to select and purify the biologically active derivatives that bind to the same targets and have an agonist or an antagonist biological activity of the SMR1-peptide of the invention are described hereunder.

The modulating agent according to the invention may be a protein, a peptide, a hormone, an antibody or a synthetic compound which is either a peptide or a non peptidic molecule, such as any compound that can be synthesized by the conventional methods of organic chemistry.

Selection of the modulating agent of the invention can be performed both in assessing the binding of a candidate ligand molecule to the NEP binding site for the QHNPR (SEQ ID NO: 1) pentapeptide, and in determining the metabolic changes induced by this candidate molecule on its target, such as the synthesis and/or release of the primary or secondary messenger metabolites as a result of a transduction signal via the protein kinases or adenylate cyclase and the activation of a protein of the G family or the variation of the enzymatic activity of NEP, specifically on the metabolism of natural NEP substrates.

Binding assays of the candidate molecule are generally performed at 4° C. to 25° C. or 37° C. In order to facilitate the reading of the hereinafter described protocol, QHNPR (SEQ ID NO: 1) pentapeptide is also used instead of or in competition with a candidate molecule.

Accordingly, another object of the present invention is a process for screening ligand molecules that specifically bind to the NEP binding site for the QHNPR (SEQ ID NO: 1) pentapeptide, comprising the steps of:

a) preparing a cell culture or an organ specimen or a tissue sample (cryosections or slices or membrane preparations or crude homogenates) containing NEP binding sites for the QHNPR (SEQ ID NO: 1) pentapeptide;

b) adding the candidate molecule to be tested in competition with half-saturating concentration of labeled pentapeptide;

c) incubating the cell culture, organ specimen or tissue sample of step a) in the presence of the candidate molecule during a time sufficient and under conditions for the specific binding to take place;

d) quantifying the label specifically bound to the cell culture, organ specimen or tissue sample in the presence of various concentrations of candidate molecule (preferably $10^{-10}$ to $10^{-5}$ M).

In said above process, a half-saturating concentration is the concentration of the labeled QHNPR (SEQ ID NO: 1) pentapeptide which binds 50% of the NEP binding sites.

This process also allows to define the relative affinity of the candidate molecule compared to the QHNPR (SEQ ID NO: 1) affinity.

Another object of the present invention is a process for determining the relative affinity of ligand molecules that specifically bind to the NEP binding sites for the QHNPR (SEQ ID NO: 1) pentapeptide comprising the steps a), b), c) and d) of the above process for each candidate molecule and further comprising the step e) of comparing the affinity of each candidate molecule quantified in step d) to the one of the other candidate molecules.

Another object of the present invention is a process for determining the affinity of ligand molecules that specifically bind to the NEP binding site for the QHNPR (SEQ ID NO: 1) pentapeptide, comprising the steps of:

a) preparing a cell culture or an organ specimen or a tissue sample (cryosections or slices or membrane preparations or crude homogenates) containing NEP binding sites for the QHNPR (SEQ ID NO: 1) pentapeptide;

b) adding the candidate molecule which has previously been labeled with a radioactive or a nonradioactive label;

c) incubating the cell culture, organ specimen or tissue sample of step a) in the presence of the labeled candidate molecule during a time sufficient and under conditions for the specific binding to take place; and d) quantifying the label specifically bound to the cell culture, organ specimen or tissue sample in the presence of various concentrations of the labeled candidate molecule (preferably $10^{-10}$ to $10^{-5}$M).

The candidate ligand molecule may be radioactively labeled ($^{32}P$, $^{35}S$, $^{3}H$, $^{125}I$ etc.) or nonradioactively labeled (biotin, digoxigenin, fluorescein etc.)

Thus, the present invention also pertains to a process for screening ligand molecules that possess an agonist activity on the NEP binding site of the QHNPR (SEQ ID NO: 1) pentapeptide, comprising the steps of:

a) preparing a cell culture or an organ specimen or a tissue sample (cryosections or slices or membrane preparations or crude homogenates) containing NEP binding sites for the QHNPR (SEQ ID NO: 1) pentapeptide;

b) incubating the cell culture, organ specimen or tissue sample of step a) at concentrations allowing measurement of NEP enzymatic activity under initial velocity conditions (e.g. as defined by the method of Example 1, Material and Methods) in the presence of the candidate molecule (preferably $10^{-10}$-$10^{-5}$ M), a half-saturating concentration of QHNPR (SEQ ID NO: 1) and a NEP substrate during a time sufficient for the hydrolysis of the NEP substrate to take place under initial velocity conditions;

c) quantifying the activity of the NEP present in the biological material of step a) by measuring the levels of NEP substrate hydrolysis, respectively in the presence or in the absence of the candidate ligand molecule and in the presence or in the absence of QHNPR (SEQ ID NO: 1).

In said above process, a half-saturating concentration is the concentration of the QHNPR (SEQ ID NO: 1) pentapeptide which reduces by half the degradation of the NEP substrate.

Another object of the present invention comprises a process for screening ligand molecules that possess an antagonist activity on the NEP binding site of the QHNPR (SEQ ID NO: 1) pentapeptide, comprising the steps of:

a) preparing a cell culture or an organ specimen or a tissue sample (e.g. cryosections or slices or membrane preparations or crude homogenates) containing NEP binding sites for the QHNPR (SEQ ID NO: 1) pentapeptide;

b) incubating the cell culture, organ specimen or tissue sample of step a) at concentration allowing measurement of NEP enzymatic activity under initial velocity conditions in the presence of a submaximal concentration of the XQHNPR (SEQ ID NO: 8) peptide, specifically the QHNPR (SEQ ID NO: 1) peptide and a NEP substrate, in the presence of the candidate molecule during a time sufficient for the hydrolysis of the NEP substrate to take place under initial velocity conditions;

c) quantifying the activity of the NEP present in the biological material of step a) by measuring the levels of NEP substrate hydrolysis, respectively in the presence or in the absence of the candidate ligand molecule and in the presence or in the absence of QHNPR (SEQ ID NO: 1).

In a preferred embodiment of said above process, a submaximal concentration is a concentration of pentapeptide which reduces by at least 50% and preferably by at least 75% the degradation of the substrate.

As mentioned above, another metabolic assay in order to assess the agonist or the antagonist activity of the candidate ligand molecule comprises the incubation of the ligand candidate in the presence of a primary cell culture or established cell line or tissue sample of rat, mouse or human origins and an endogenous or exogenous NEP substrate and determining, either or both quantitatively and qualitatively, the hydrolysis of the NEP substrate.

A preferred tissue sample that is used in the screening methods according to the present invention is a membrane preparation or slices of spinal cord from rats, a tissue known to be appropriated for NEP activity measurement.

Such a procedure can also be applied to tissues and/or cells of mouse or human origin or cell lines transfected with human NEP cDNA.

In the methods according to the invention, the peptides or peptidomimetics according to the invention may be administered by any of a variety of means. In certain preferred embodiments, administration may be parenteral, most preferably intravenous. In other preferred embodiments, administration may be intranasal, oral, sublingual, transmucosal, intrarespiratory, or through an inert or iontophoretic patch.

Dosages of the peptide or peptidomimetic to be administered will depend on the particular patient, the condition, and the route of administration, and can be determined empirically by the reduction or elimination linked to the pathological disorders listed above in response to an elevating dosage regimen. Preferred dosages are from about 0.1 µg/kg to about 1 mg/kg, more preferably from about 1 µg/kg to about 100 µg/kg, and most preferably from about 1 µg/kg to about 50 µg/kg.

Central Nervous System Disorders

The present invention focuses on the prevention or treatment of Central Nervous System (CNS) disorders giving rise to mental disorders in mammals.

For purposes of the invention, the term "mammal" is used in its usual taxonomic sense and specifically includes humans.

The CNS disorders of the present invention refer to mental disorders including impaired interpersonal and behavioral disorders.

Various mental disorders are described in the PCT patent application WO 01/00 221. The present invention provides a new therapeutic pathway to reduce or eliminate symptoms of a mental disorder.

As used herein, "having a mental disorder" means manifesting at least one clinically observable behavior or physical characteristic that is generally recognized as a symptom of a mental disorder. The term "to reduce or eliminate symptoms of a mental disorder" means to obtain a clinically observable beneficial change in one or more behavior or physical characteristic that is generally recognized as a symptom of a mental disorder. Mental disorders are diagnostic categories for which criteria are provided by a manual written by working groups of psychiatrists. This manual is published by the American Psychiatric Association, "Diagnostic and Statistical Manual of Mental Disorders", 1992. Each of the disorders discussed below are well known, as evidenced by their treatment in this manual. Thus, only brief definitions are provided herein for the disorders discussed below.

In certain preferred embodiments, the mental disorder is an avoidance disorder. As used herein, an "avoidance disorder" means a disorder having as an essential feature a pervasive pattern of social discomfort, fear of negative evaluation, and timidity. It includes excessive shrinking from contact with unfamiliar people. The present invention particularly relates to avoidant disorder personalities defined as pervasive pattern of social inhibition", feeling of inadequacy, and hypersensitivity to negative evaluation, beginning by early adulthood and present in a variety of contexts (DSMP-IV-TR coded 301.82, p 718-21 of Diagnostic and Statistical Manual of Mental Disorders, American Psychiatric Assoc., 1992).

In certain preferred embodiments, the mental disorder is a decreased awareness disorder. As used herein, a "decreased awareness disorder" means a disorder marked by lack of awareness of the existence or feelings of others (e.g. treats a person like if he or she were a piece of furniture; does not notice another person's distress). These disorders can be elements of an autistic disorder.

In certain preferred embodiments, the mental disorder is an attention deficit/hyperactivity disorder. As used herein, an "attention deficit disorder" means a disturbance in which the predominant feature is the persistence of developmentally inappropriate and marked inattention. Deficit/hyperactivity disorders also include combined type, predominantly inattentive type, and hyperactive-impulsive type (DSMP-IV-TR coded 314.01, 314.00, 314.01, p 87-93 of Diagnostic and Statistical Manual of Mental Disorders, American Psychiatric Assoc., 1992).

In certain preferred embodiments, the mental disorder is an arousal disorder. As used herein, an "arousal disorder" means a reactive attachment disorder such as persistent failure to initiate or respond to most social interactions. This can lead to severe forms in children that have been called "failure to thrive" or "hospitalism". Decreased interest in environment is another element of reactive attachment disorders, commonly manifested as insufficient visual tracking of eyes, faces or voices, absence of reaching out to objects.

In certain preferred embodiments, the mental disorder is impaired interpersonal functioning and relationship to the external world. As used herein, "impaired interpersonal functioning and relationship to the external world" means other interpersonal problems, examples of which are difficulties with co-workers or with romantic partners. These disorders include schizoid personality disorder, which is a pervasive pattern of indifference to social relationships and a restricted range of emotional experience and expression, and also include schizophrenia or depressive disorder.

In certain preferred embodiments, the mental disorder is a mood disorder, with special reference to dysthymic disorder (mental coded 300.4, p 380-1 in Diagnostic and Statistical Manual of Mental Disorders, American Psychiatric Assoc., 1992), and depressive disorder no otherwise specified (mental, p 381-2 in Diagnostic and Statistical Manual of Mental Disorders, American Psychiatric Assoc., 1992); cyclothymic disorder and bipolar disorder not otherwise specified (mental coded 301-13 and 296.80, respectively, p 400 in Diagnostic and Statistical Manual of Mental Disorders, American Psychiatric Assoc., 1992).

In certain preferred embodiments, the mental disorder is impaired social activity linked to sexuality. As used herein, "impaired social activity linked to sexuality" is impairment of social relationship to a sexual partner, which can lead to impairment of occupational functioning.

In certain preferred embodiments, the mental disorder is impaired sexual behavior. As used herein, "impaired sexual behavior" includes sexual and gender identity disorders with special reference to hypoactive sexual desire disorder (H.S.D.D., mental coded 302.71, p 543-4 in Diagnostic and Statistical Manual of Mental Disorders, American Psychiatric Assoc., 1992), defined as persistently or recurrently deficient or absent sexual fantasies and desire for sexual activity, and further includes feelings of inadequacy concerning sexual performance such as untimely ejaculation.

In certain preferred embodiments, the mental disorder is simple phobia (mental coded 300.29, p 443-9), social phobia (mental coded 300.23, p 450), obsessive-compulsive disorder (mental coded 300.3, p 456-63), or acute stress disorder (mental coded 308.3, p 471-2), according to the references of Diagnostic and Statistical Manual of Mental Disorders, American Psychiatric Assoc., 1992.

In certain preferred embodiments, the mental disorder further relates to pain disorders, either associated with psychological factors, or with both psychological factors and a general medical condition or with a general condition (mental coded 307.80, p 499-503 in Diagnostic and Statistical Manual of Mental Disorders, American Psychiatric Assoc., 1992).

In certain preferred embodiments, the mental disorder comprises symptoms of more than one of these disorders.

The present invention is illustrated in details in the following figures and examples without being in any way limited in scope to these specific embodiments.

BRIEF DESCRIPTION OF THE DRAWINGS

FIG. 1-B: Time course of Substance P hydrolysis (12.5 nM) by rat spinal cord membrane preparations in the presence or absence of different peptidase inhibitors at 10 μM final concentration:—an ACE inhibitor, captopril,—the CPB and DPPIV inhibitors, GEMSA and DPPIV inhibitor. Each point represents the percent of 3H-substance P hydrolyzed by 250 μg membrane proteins incubated at 25° C. in a 250 μl final volume of Tris/HCl buffer.

Values represent the concentration of intact and immunoreactive Met-enkephalin (mean of 2 determinations) determined by RIA analysis (μM) and recovered after 20 min. incubation at 25° C. with 1 mg fresh tissue slices in a 1 ml final volume of KRBG buffer (2-A) and the quantity of intact Met-enkephalin (mean of 2 determinations) determined by RP-HPLC analysis (peak height at 18.9 min. Retention time) recovered after 20 min. incubation at 25° C. with 1 mg fresh tissue slices in a 1 ml final volume of KRBG buffer (2-B).

Figure 3A:
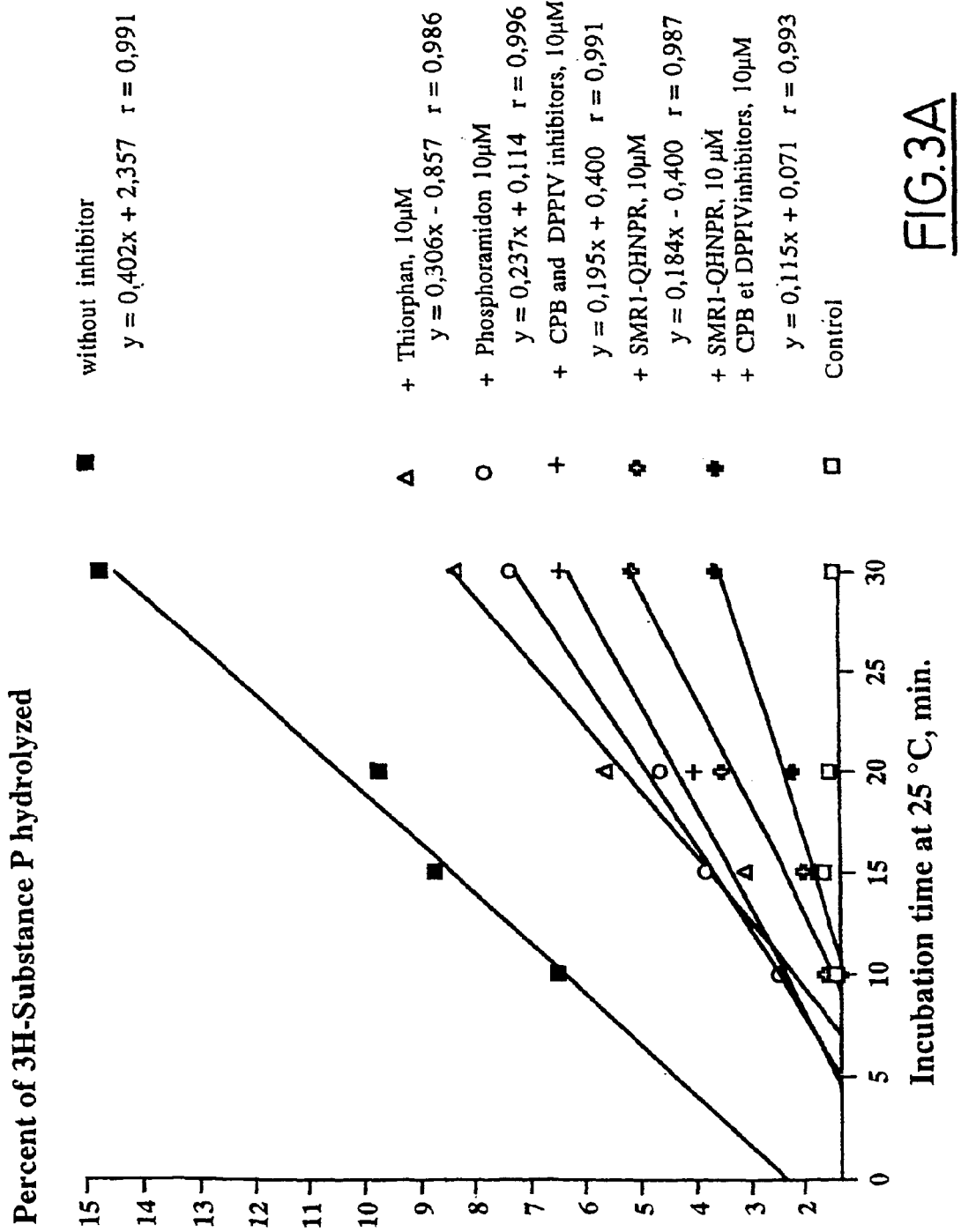
Figure 3B:
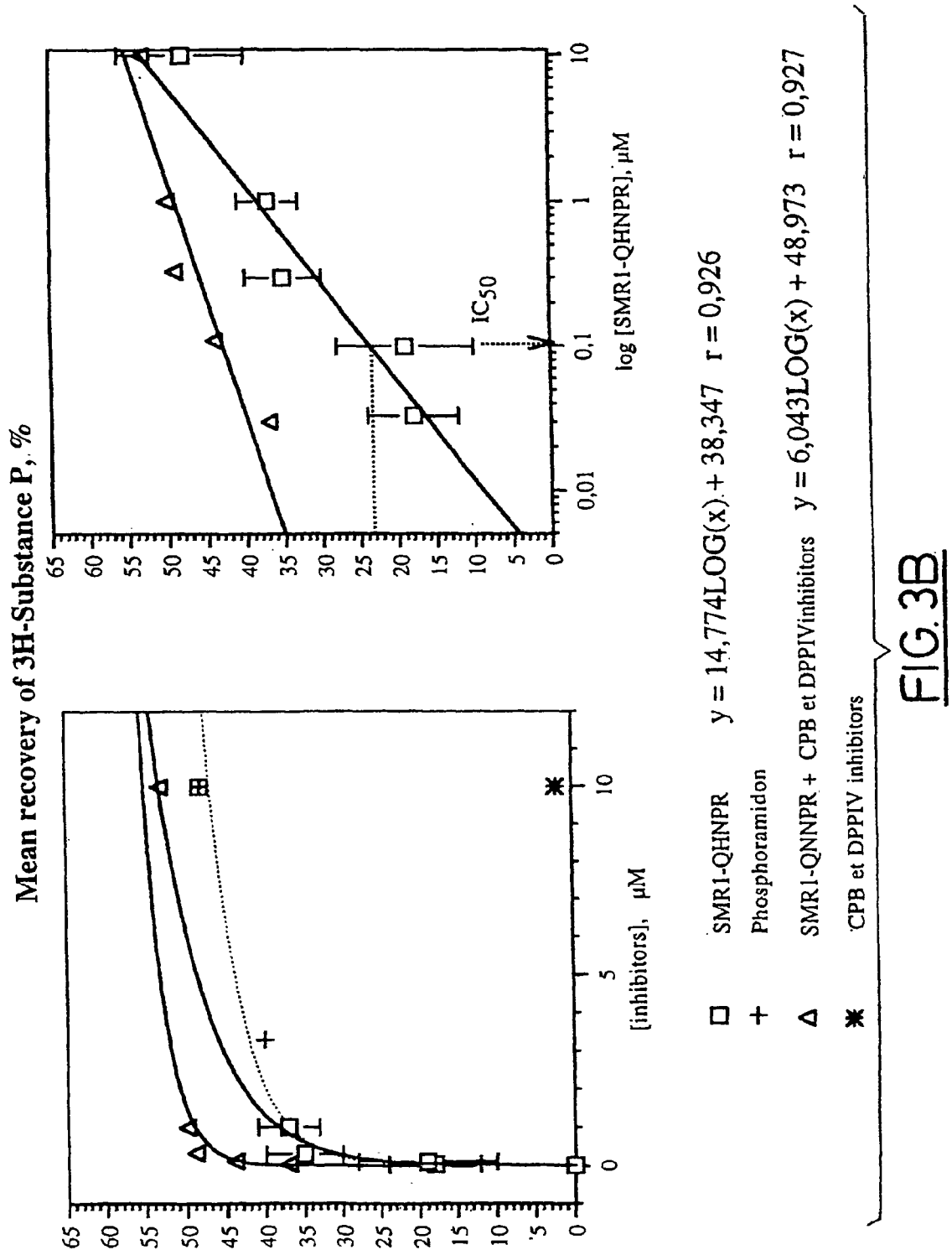

FIG. 3-A: Substance P hydrolysis (25 nM) by rat spinal cord slices, in the presence or absence of different peptidase inhibitors at 10 μM final concentration:—a NEP inhibitor, Phosphoramidon,—a NEP inhibitor, Thiorphan,—the CPB and DPPIV inhibitors, GEMSA and DPPIV inhibitor,—the SMR1-QHNPR (SEQ ID NO: 1) alone or combined with CPB and DPPIV inhibitors. Control represents the 3H-substance P hydrolysis in absence of tissue slice. Each point represents the percent of 3H substance P hydrolyzed by 1 mg fresh tissue slices incubated at 25° C. in a 1 ml final volume of KRBG buffer.

FIG. 3-B: Concentration-dependent inhibition by SMR1 QHNPR (SEQ ID NO: 1) of 3H-Substance P (12.5 nM) catabolism by rat spinal cord membrane preparations. Comparison with—a NEP inhibitor, Phosphoramidon and,—CPB and DPPIV inhibitors, GEMSA+DPPIV inhibitor. Comparison between the inhibitory activity exerted by QHNPR (SEQ ID NO: 1) peptide alone or in combination with CPB and DPPIV inhibitors. Each point represents the mean recovery (in percentages) of intact 3H-substance P after 10 min; incubation at 25° C. with 250 μg membrane protein in 250 μl Tris/HCl buffer (mean of 2 determinations).

Figure 4:
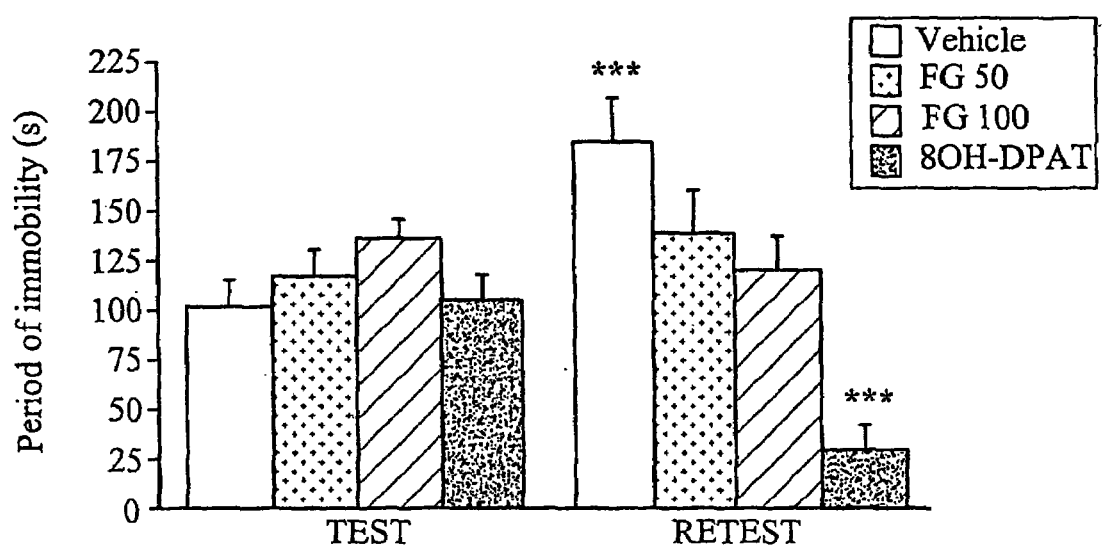

FIG. 4: Graphic representation of the periods of immobility during the test and the retest in the Behavioral Despair test.

EXAMPLES

Example 1

Ex Vivo, Exploration of the Functional Consequences Resulting from the Interaction of SMR1-OHNPR Peptide with NEP The consequences of the protection of exogenous NEP-sensitive peptides by SMR1-Pentapeptide, in the extracellular levels of Met-Enkephalin and Substance P have been assessed using membrane preparations and fresh slices of rat nervous tissues.

1. Materials and Methods 1.1. Animals and Tissue Preparations

Sexually mature (from 7 to 9 weeks) male Wistar rats (Iffa Credo), were used. Up to the day of experiment, the rats were kept under conditions of constant ambient temperature (24° C.) and of cycled light (on 8 h/off 20 h) with distribution of food and water ad libitum. On the day of the experiment, the animals were sacrificed by cardiac puncture under pentobarbital (Sanofi, 45 mg/kg body weight, i.p.) or ketamine (Imalgene 500, Rhone Merieux, 150 mg/kg body weight, i.p.) anesthesia or alternatively by carbon dioxide asphyxia.

Slices of Fresh Tissue

The organs are rapidly removed, dissected on ice, freed of nerve fibers and of adipose tissues and then washed in cold oxygenated glucose—and bicarbonate—containing Krebs Ringer (KRBG) solution, whose composition is the following: 120 mM NaCl-5 mM KCl-1.2 mM $KH_2PO_4$-27.5 mM $NaHCO_3$-2.6 mM $CaCl_2$-0.67 mM $MgSO_4$-5.9 mM glucose. The slices of tissues are prepared either manually with the aid of a scalpel (1-2 mm thick), or mechanically with the aid of a "Tissue Chopper" (1 mm thick). Slices are then dispersed into reaction tubes where they are subjected to three successive washes in ice-cold oxygenated KRBG. Thereafter, they are kept at 4° C. in the same buffer supplemented with 10 μM Bestatin (a membrane aminopeptidase, (APN), inhibitor, Roche) and oxygenated under an atmosphere of 95% O2-5% CO2 until used immediately, as enzyme source.

Membrane Preparations

The organs dissected out and washed in ice-cold KRBG are homogenized at 4° C. in 10 volumes (vol./wt.) of 50 mM Tris/HCl buffered at pH 7.2, using a Teflon-glass homogenizer (3×5 sec.). A first centrifugation of 5 min. at 1000×g and 4° C. makes it possible to remove the tissular debris and the nuclei in the pellet. A second centrifugation of the supernatant at 100 000×g and 5° C. concentrates the membrane fraction into the pellet, which will be superficially washed three times with cold Tris/HCl buffer and resuspended in fresh buffer using a Kontes homogenizer, aliquoted and stored at −80° C. while waiting to be used as enzyme source, at least until three months.

1.2 Protein Determination

For the determination of the tissue and membrane protein concentrations, the Bio-Rad DC protein assay (Bio-Rad), was used. As with the Lowry assay, the Bio-Rad kit is based on the reaction of sample protein content with an alkaline copper tartrate solution and Folin reagent. The absorbance is read at 750 nm from 15 min. to 2 h. after the addition of reagent. The calibration curve is prepared from dilutions of a standard solution of BSA (Bovine Serum Albumin) from 0.2 to 1.44 mg/ml protein.

1.3. Measurement of the NEP Enzymatic Activity 1.3.1. NEP Source—Substrates and Inhibitors For the experiments of analysis of the NEP peptidase activity, an ex vivo model using incubations of membrane and fresh tissue slice preparations from nervous tissues that are known to be appropriate for exploring NEP peptidase activity: i.e. the dorsal zone of rat spinal cord, was first developed. The metabolism rate of the NEP-sensitive peptides was measured using the both NEP substrates involved in the signaling of the nociceptive response: the neuropeptides Met-enkephalin and Substance P. Native Met-enkephalin (Peninsula, 10 μM) and modified tritiated Substance P: [(3,4$^3$H) Pro$^2$-Sar$^9$-Met(O$_2$)$^{11}$]-Substance P with a specific radioactivity of 40 Ci/mmol. (NEN, 12.5-25 nM) were used.

The objective was to measure the NEP-specific endoproteolysis of these substrates. For that, in each test, the hydrolysis of substrate was analyzed both in the presence and in the absence of specific synthetic inhibitors of NEP (10 μM Phosphoramidon, Roche and/or 1-10 μM Thiorphan, Sigma), and in all cases in the presence of an inhibitor of APN, the Bestatin (10 μM). Furthermore, for studying the functional role of SMR1-QHNPR (SEQ ID NO: 1), the reaction was carried out in the presence of the SMR1-peptide alone or combined with specific inhibitors of membrane peptidases which could inactivate the QHNPR (SEQ ID NO: 1) peptide by cleaving its C-terminal end: an inhibitor of carboxypeptidase B (GEMSA, 10 μM, Sigma) and an inhibitor of dipeptidylpeptidase IV (DPPIV inhibitor, 10 μM, Roche).

1.3.2. The Enzymatic Activity Assay

Slices of Fresh Tissue

In the first instance, sections of fresh tissue are preincubated in KRBG medium containing 10 μM bestatin, at 25, 30 or 37° C. in a constantly shaken water bath and under an atmosphere of 95% O2-5% CO2, in the presence or in the absence of NEP inhibitor. At the end of the preincubation period (15 min.), the medium is replaced with fresh medium containing the substrate alone or combined with NEP inhibitor or SMR1-QHNPR (SEQ ID NO: 1) and the incubation is carried out at the same incubation conditions as the preincubation. At the end of the incubation period (from 5 to 30 min.), the medium is transferred to ice-cold tubes containing hydrochloric acid, such as the final concentration of HCl will be 0.1 N. Samples are kept at −30° C. until the measurement of their intact substrate and its metabolites content.

The temperature and time of incubation as well as the concentration of substrate and of tissue enzyme are defined according to the results such as the NEP hydrolysis activity will be measured under conditions of initial velocity.

Membrane Preparations

The membrane preparations are preincubated in 50 mM Tris/HCl buffered at pH 7.2 and containing 10 μM Bestatin, at 25, 30 or 37° C. in constantly shaken water, in the presence or in the absence of NEP inhibitor. At the end of the preincubation period (10 min), the substrate is added alone or combined with NEP inhibitor or SMR1-QHNPR (SEQ ID NO: 1) and the incubation is carried out at the same incubation conditions as the preincubation. At the end of the incubation period, the reaction is stopped by cooling to 4° C. and adding to hydrochloric acid such as the final concentration of HCl will be 0.3 N. Samples are kept at −30° C. until the measurement of their intact substrate and its metabolites content.

The temperature and the time of the incubation as well as the concentration of substrate and of membrane enzyme are defined according to the results such as the NEP hydrolysis activity will be measured under conditions of initial velocity.

1.3.3. The Detection of the Substrate and its Metabolites

To separate, detect and quantify the intact substrate and its metabolites, various techniques (depending on whether the substrate was radiolabeled or not), were used: two are based on the principle of reverse-phase chromatography for the selective isolation of the products of the reaction (C-18 Sep-Pak cartridges and RP-HPLC) and the third is based on the specific detection of the substrate by radio-immunoassay (RIA).

The C-18 Sep-Pak Cartridges

The C-18 Sep-Pak cartridges (Waters) were used to analyze the hydrolysis of the radiolabeled peptides: they separate compounds according to their differences in polarity. This solid-phase extraction procedure allows isolating the substrate from its metabolites, since the hydrophobic character of the peptide metabolites is reduced or even lost compared to the intact peptide substrate.

3H-Metabolites of radiolabeled substance P are eluted in two steps: one with $H_2O$ −0.1% TFA and the second one with 20% methanol −0.1% TFA, while the intact 3H-substance P is eluted in the third step with 70-100% methanol-0.1% TFA. The radioactivity of eluted and isolated compounds is determined by liquid scintillation spectrometry.

RP-HPLC (Reverse Phase High Performance Liquid Chromatography)

HPLC is a highly resolutive procedure that allows one to isolate, and detect by coupled spectrophotometer analysis, the non-radioactive peptides whose concentration is at least 1 to 10 μM. The C-18 RP-HPLC is based on the same principle as the C-18 Sep-Pak cartridge. The chromatographic analyses were used to study the hydrolysis of Met-Enkephalin, that were done on a C-18 LUNA analytical column (150×4.6 mm inner diameter, AIT) packed with 5 μm-diameter beads.

RP-HPLC performed with a one-step 30-minute linear gradient ranging from H2O −0.1% TFA to 100% acetonitril −0.1% TFA, at a 1 ml/min flow rate, leads to a resolutive separation of the two Met-Enkephalin metabolites and of the intact substrate. Their identification and relative quantification (peak height) are checked by continuously monitoring the UV absorbance at 254 nm of column outflow.

RIA Assay (Radio-Immuno-Assay)

RIA is a fine analytical method, which allows quantifying compounds, whose concentration is between 1 and 100 nM or even less. Herein, a competitive RIA system has been used: the quantity of radioactive antigen bound to the antibody decreases in a manner inversely proportional to the quantity of antigen contained in the standard solution or in the sample. The free radioactive antigen is separated from the radioactive antigen—antibody complex by immuno-precipitation.

The activity of enkephalinase NEP is monitored by quantification of the disappearance of the initial Met-enkephalin substrate. The first antibody used is a rabbit antibody directed against the C-terminal end of Met-enkephalin (cross—reactivity with metabolites or other peptides is <1%) (Goros et al, J. Neurochem. (1978), 31; 29-39. Radio immunoassay of methionine and leucine enkephalins in regions of rat brain and comparison with endorphins estimated by a radioreceptor assay). The second antibody is a horse antibody directed against the rabbit immunoglobulins. The radiolabeled antigen is iodinated Met-enkephalin ($^{125}$I-Met-Enk enkephalin) with a specific radioactivity estimated at 3000 Ci/mmol.

Briefly, the Met-enkephalin RIA is performed in 100 mM Tns/HCl buffered at pH 8.6 and containing 0.1% BSA and 0.1% Triton X 100. Standard (1-100 rdM) or sample (100 μl), diluted anti-Met-Enkephalin antibody (100 μl, 1/2000) and $^{125}$I-Met-Enk (10000 cpm, 100 μl) are incubated overnight at 4° C. Bound and free fractions are separated by immunoprecipitation with the second anti-rabbit immunoglobulin in presence of polyethylene glycol 6000 (6%). After centrifugation the bound radioactivity of the precipitate is quantified using a gamma-spectrometer.

2. Results

To specify the inhibitory role of the SMR1-QHNPR (SEQ ID NO: 1) on the NEP enzymatic activity, it was necessary to first develop an experimental protocol allowing to perform the hydrolysis of Substance P or Met-Enkephalin peptides under conditions of initial velocity measurement.

2.1. Search for Experimental Conditions of Initial Velocity Measurement of NEP Endopeptidase Activity 2.1.1. Hydrolysis of Native Met-Enkephalin In first series of experiment, the slices and the membrane preparations of spinal cord tissues were incubated at 30° C. in a 1 ml final volume of KRBG, and at 37° C. in a 0.25 ml final volume of Tris/HCl 50 mM, pH 7.2, respectively.

RP-HPLC Analysis

The calibration of the RP-HPLC chromatographic system reveals that marker Met-enkephalin is eluted at a retention time of 18.8 min. In the case of the samples, a peak is identified whose height increases considerably in the presence of a NEP-specific inhibitor: this peak, whose retention time is 18.8±0.2 min., corresponds to the intact Met-enkephalin substrate. Conversely, two peaks having retention times of 5.8±0.2 min. and 12.8±0.1 min., corresponding to the metabolites Tyr-Gly-Gly and Phe-Met respectively, appear in the absence of NEP-inhibitors. This result indicates that spinal tissue enzyme has cleaved the substrate predominantly at the $Gly^3$-$Phe^4$ amide bond of the peptide, which already corresponds to enkephalinase activity.

At the level of membrane preparations as well as of fresh tissue slices, a high NEP-specific hydrolysis of the exogenous Met-enkephalin is observed during the 10 min. incubation at 37° C.: the spinal cord enkephalinase activity provokes a disappearance of the Met-enkephalin peak and that is reversed in the presence of 10 μM Phosphoramidon or 1 μM Thiorphan (80-90% inhibition). In addition, under these conditions, both specific NEP inhibitors ensure the almost complete inhibition of enkephalinase activity over the time of incubation at 37° C., from 10 to 30 min.

Since, the maximum hydrolysis was undoubtedly reached, at 37° C. temperature within the 10 min. incubation, in the next experiments the incubation temperature has been subsequently reduced to 30° C. then to 25° C. Effectively, for the fresh tissue slices incubated at 30° C., the level of hydrolysis of Met-enkephalin increases with time (from 0 to 30 min.). In the same manner, for the membrane preparations incubated at 30° C., it is also possible to note an increase in the level of hydrolysis in relation to the enzyme concentration (from 0 to 2 mg/ml). However, no clear linear relationship could be established.

Indeed, the HPLC chromatography coupled to spectrophotometer analysis is a semi-quantitative technique and the single measurement of the heights or areas of peaks is not sufficiently precise to calculate quantitative proportional relationships. Then, to precisely quantify the Met-enkephalin, a specific quantitative RIA detection was used.

2.1.2. Hydrolysis of Modified Tritiated Substance P

The experimental parameters which allow to study, under conditions of initial velocity measurement, the hydrolysis of the substrates, Met-enkephalin and Substance P, by nervous tissue-containing NEP, have been established.

Figure 1A:
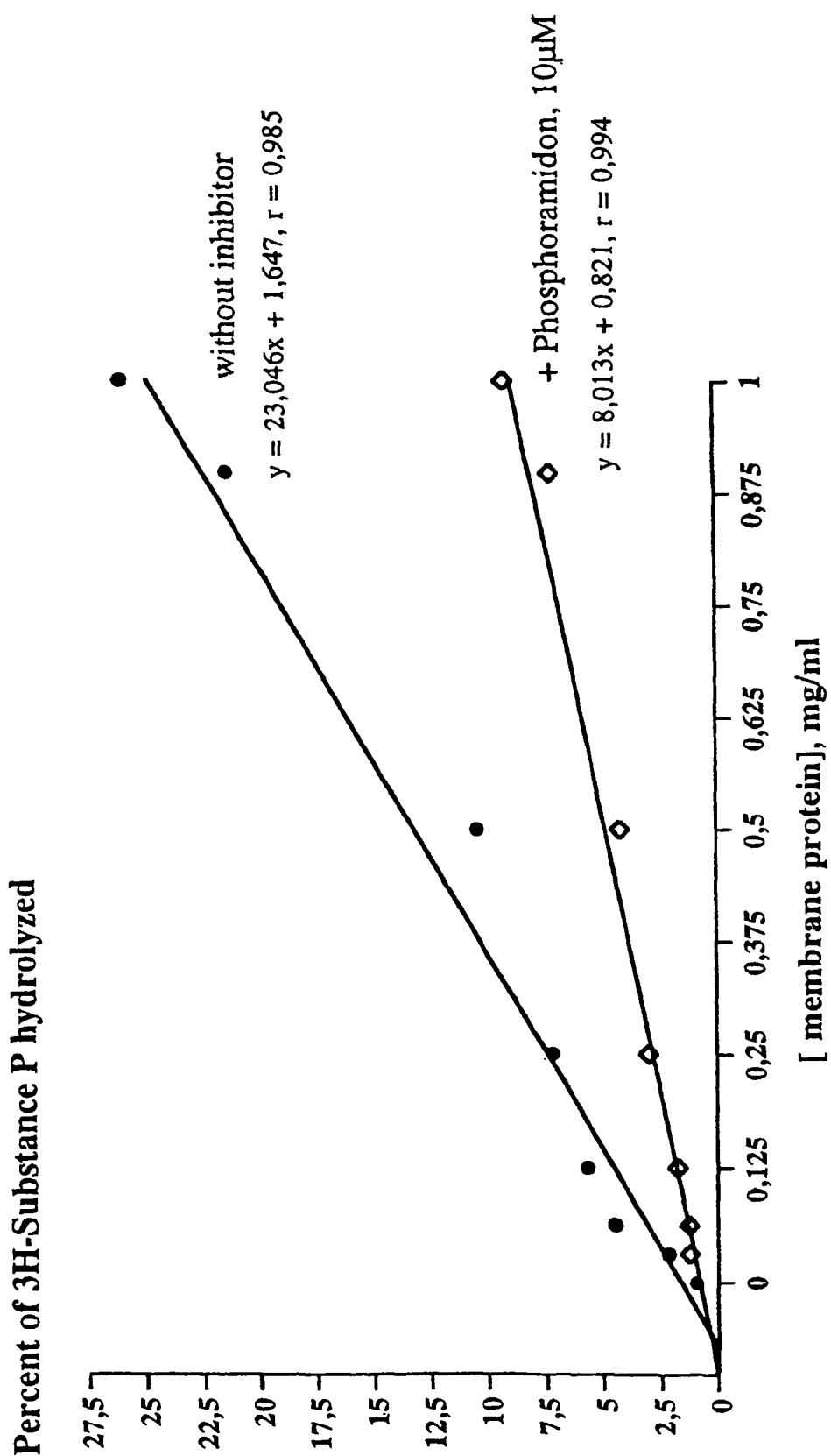
FIG. 1-A: Influence of spinal cord membrane protein concentration on Substance P hydrolysis (25 nM) in the presence or absence of the synthetic NEP inhibitor, Phosphoramidon, 10 μM. Each point represents the percent of 3H-substance P hydrolyzed by spinal cord membrane incubated 15 min. at 30° C. in a 250 μl final volume of Tris/HCl buffer.
Figure 1B:
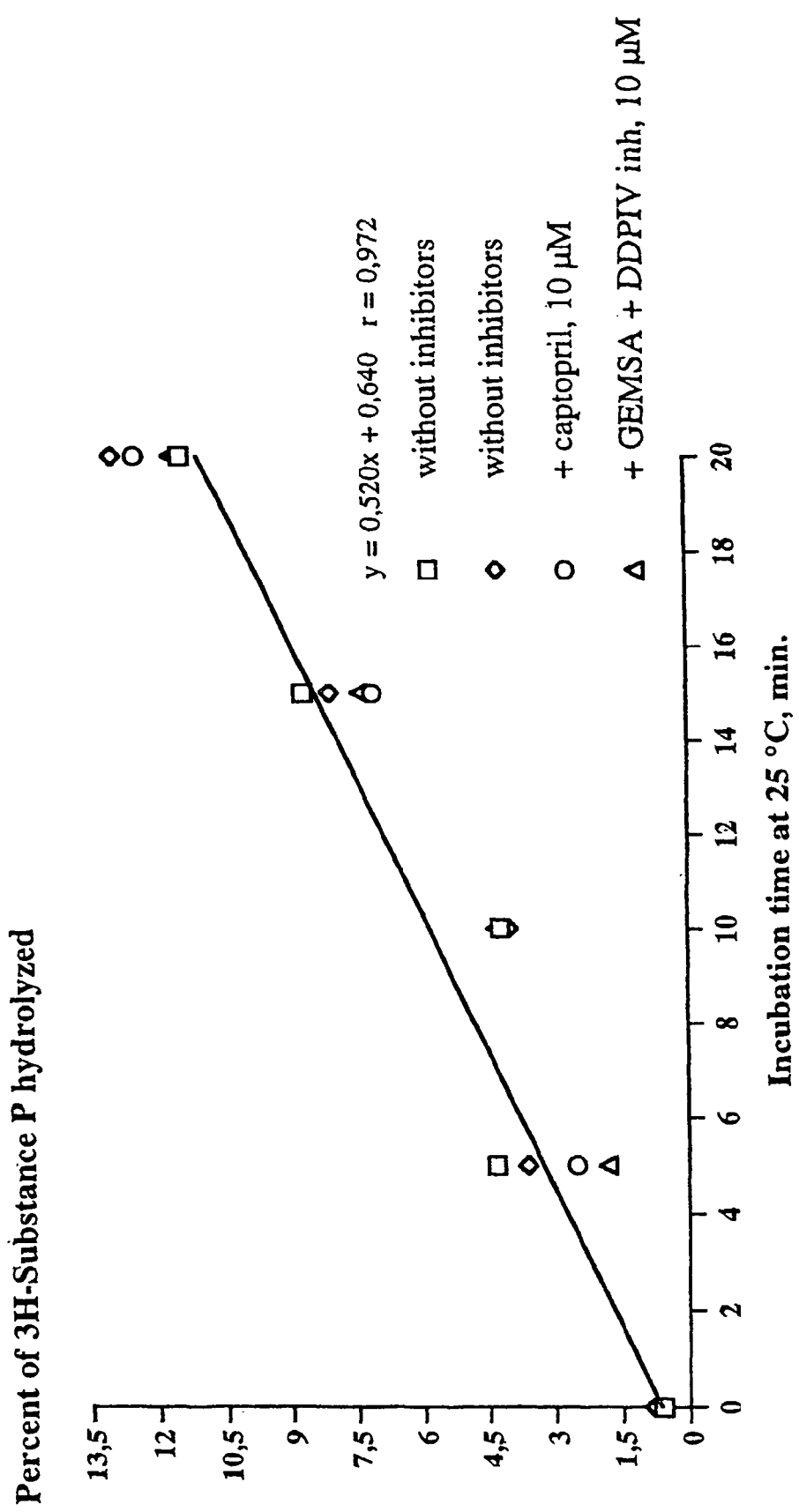

In that respect, the influence of the membrane protein concentration of rat spinal cord (from 0.03 to 1 mg/ml, final concentration) on the level of the Substance P hydrolysis (25 nM), after 15 min. incubation at 30° C., was first tested. As illustrated in FIG. 1-A, the levels of the 3H-Substance P degradation, expressed in percent of initial substrate concentration, increase proportionally from 2 to 25% in a linear related-function to membrane protein concentration. A close correlation of r=0.98, n=7 was found in the absence and, of r=0.99, n=7 in the presence of 10 μM Phosphoramidon. Furthermore, in the same experimental condition, the addition of Phosphoramidon results in a clear reduction of the Substance P degradation (50 to 65% protection of exogenous peptide).

Similarly, the level of Substance P hydrolysis (12.5 nM) as a function of the incubation time at 25° C. (5-20 min) was also studied. The membrane protein concentration chosen was 1 mg/ml. The Substance P catabolism by spinal cord membranes increases linearly with the time of incubation, with a close correlation of r=0.97, n=18 (FIG. 1-B). Captopril, (10 μM) a potent inhibitor of the Angiotensin Converting Enzyme (ACE) which also cleaves the Substance P, has no effect on the activity of the enzyme membrane preparations, as well as, for the potent inhibitors of CPB and DPPIV enzymes (protective compounds of the C-terminal SMR1-QHNPR (SEQ ID NO: 1) potential catabolism).

The conditions of initial velocity measurement of the Substance P hydrolysis by spinal cord tissue containing-NEP therefore appear to be established. However, the activity of both NEP inhibitors (Phosphoramidon and Thiorphan), does not appeared to be proportionally stable as a function of the incubation duration. Accordingly, the effect of the SMR1-QHNPR (SEQ ID NO: 1) peptide on the NEP activity will be systematically studied in relation to the time of incubation.

2.1.3. Record

The experimental conditions that allows one to study, under initial velocity measurement, the Met-enkephalin and Substance P catabolism by spinal tissues ex vivo, are reported in the table hereunder.

| | |
|---|---|
| Preincubation time | 10 mm (membrane preparations) |
| | 15 mm (fresh tissue slices) |
| Incubation times | 5 min to 30 min. |
| Tern erature | 25° C. |
| Final concentration of membrane or tissue totem s inal cord | 1 mg/ml |
| Substrate concentration | Substance P: 12.5 nM |
| | Met-enkephalin 10 μM (HPLC) |
| | 20 nM (RIA) |
| Reaction volume | 1 ml (fresh tissue slices) |
| Technique for separating the Metabolites | Sep-Pak + Liquid scintillation counter (3W-Substance P) |
| | RP-HPLC and HA (Met-enkephalin) |
| Buffer | Tris/HCl 50 mM, pH 7.2 + BSA 0.1% + Bestatln 10 μM (membrane preparations) |
| | KRBG + BSA 0.1% + Betastatin 10 μM Oxygenated under 95% $O_2$ – 5% $CO_2$ (Fresh tissue slices) |

2.2 Study of the Functional Consequences Resulting from the Interaction of the SMR1-OHNPR (SEQ ID NO: 1) Peptide with NEP 2.2.1 Degradation of Met-Enkephalin by NEP Spinal Cord The effect of a fixed concentration of SMR1-QHNPR (SEQ ID NO: 1) (10 μM) on the Met-enkephalinase activity of spinal cord slices under experimental conditions defined in paragraph 2.1.3, was first tested.

RP-HPLC Analysis

Figure 2A:
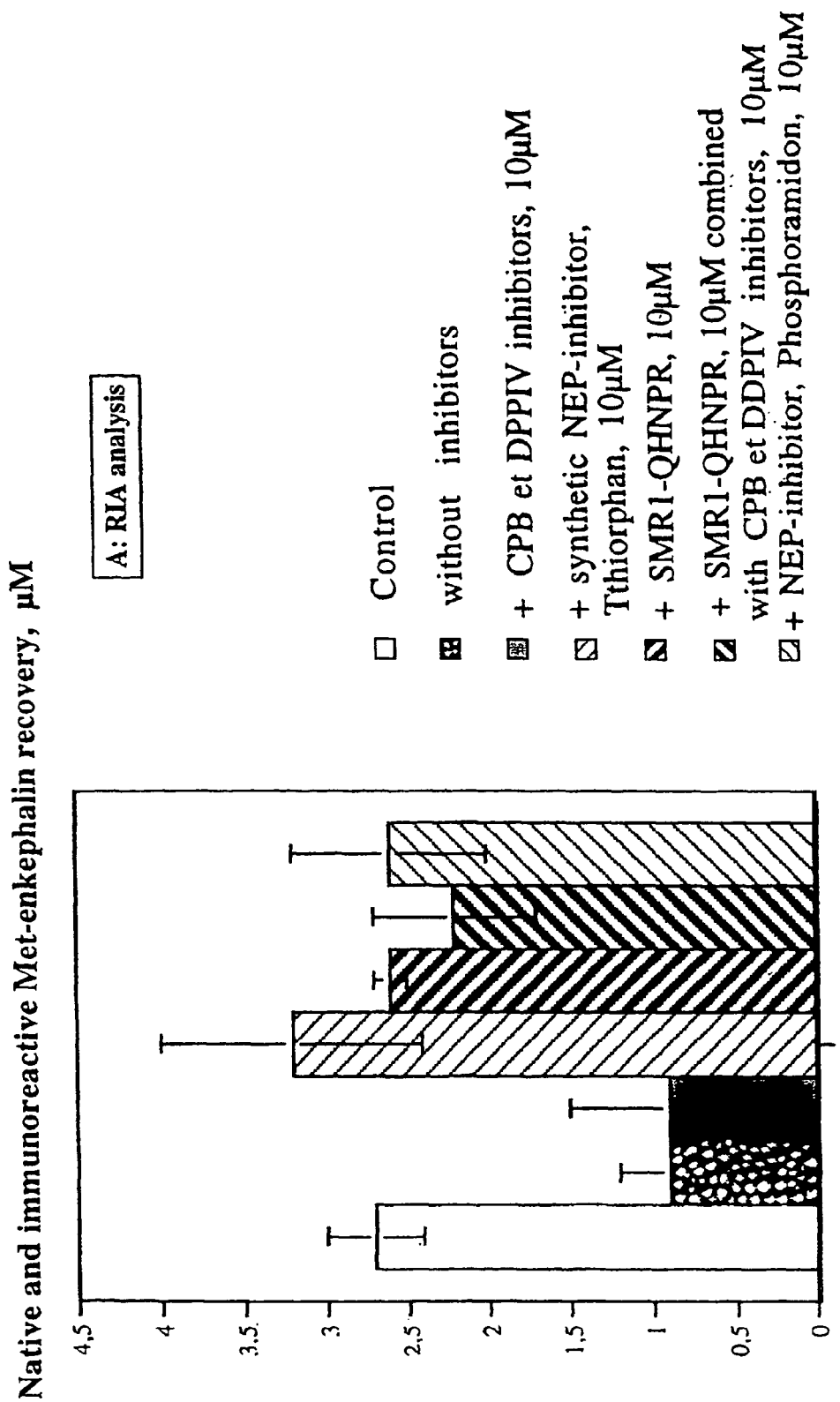
FIGS. 2-A and 2-B: Met-enkephalinase activity in spinal cord slices, in the presence or absence of different peptidase inhibitors at 10 μM final concentration:—a NEP inhibitor, Phosphoramidon,—a NEP inhibitor, Thiorphan,—the CPB and DPPUV inhibitors, GEMSA and DPPUV inhibitor,—the SMR1-QHNPR (SEQ ID NO: 1) alone or combined with CPB and DPPIV inhibitors. Control represents the Met-enkephalin recovery in the absence of tissue slice.
Figure 2B:
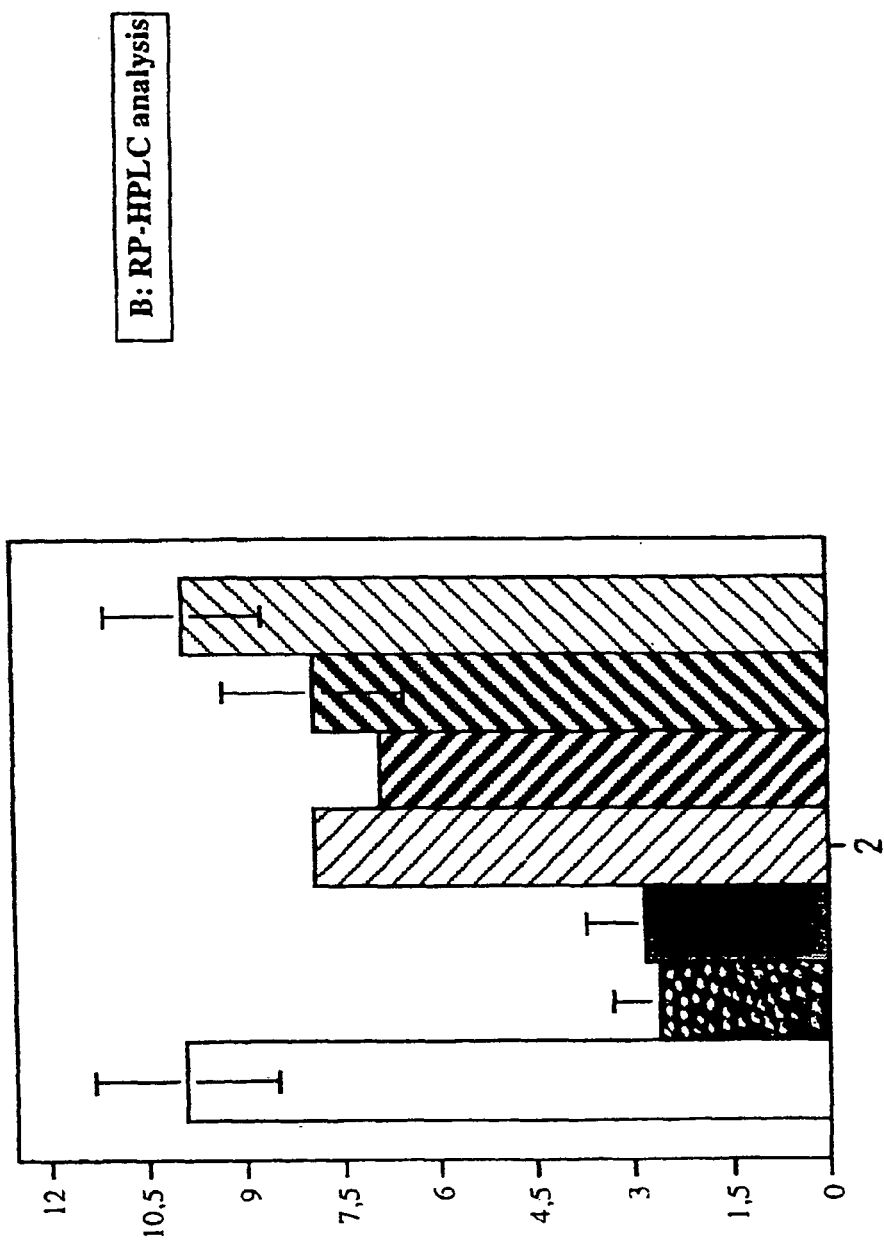

As illustrated in FIG. 2-B, the HPLC analyses show a strong NEP-specific hydrolysis of the Met-enkephalin substrate by spinal cord slices within the 20 min. incubation at 25° C. Phosphoramidon at a concentration of 10 μM ensures the complete inhibition of Met-enkephalinase activity and addition of Thiorphan (10 μM) results in a clear reduction by 80% of the Met-enkephalin degradation.

In the same experiment, the QHNPR (SEQ ID NO: 1) peptide, at 10 μM concentration, alone or combined with the inhibitors of CPB and DPPIV proteases, has an inhibitory activity of 70 or 80%; thus the SMR1-Pentapeptide is able to enter into competition with the enkephalin-pentapeptide for the NEP binding sites, both being in equal concentrations. As in case of Substance P degradation by spinal membrane preparations, the inhibitors of CPB and DDPIV alone do not have any intrinsic inhibitory activity on the Met-enkephalin degradation by fresh spinal slices. Furthermore, they apparently are no need for protecting SMR1-QHNPR (SEQ ID NO: 1) itself, especially at its C-terminal end, from the peptidase activity potentially present in slices of fresh spinal tissue.

In order to finely quantify the NEP activity and inhibition, the same experiment has been analyzed with the aid of the specific Met-Enkephalin RIA.

RIA Assay

As a whole, the crude results obtained by the reverse phase-HPLC technique are confirmed by those derived from RIA assay (FIG. 2-A). Within the 20 min incubation period at 25° C., the Phosphoramidon, Thiorphan, as well as SMR1-QH-NPR (SEQ ID NO: 1) appear as very potent compounds for protecting Met-enkephalin from NEP degrading activity. Thus, at concentration of 10 µM, they almost totally prevented the degradation of 10 µM Met-enkephalin by fresh spinal cord tissue: 96%, 100% and 96% protection, respectively.

In conclusion, all these results show the negative regulatory role exerted by the SMR1-QHNPR (SEQ ID NO: 1) peptide on the Met-enkephalinase activity of rat nerve tissues, ex vivo.

2.2.2 Degradation of Substance P by NEP Spinal Cord

SMR1-QHNPR (SEQ ID NO: 1), an inhibitor of the NEP Activity on Substance P Catabolism In a first instance, the effect of QHNPR (SEQ ID NO: 1) peptide on the hydrolysis of Substance P was searched as it was already done in relation to Met-enkephalin. For that, spinal cord slices were used and a kinetic over a 30-min. incubation period was performed under the conditions of initial velocity measurement defined in 2.1.3.

As illustrated in FIG. 3-A, Substance P hydrolysis reaction effectively takes place under initial velocity conditions: a close relationships of r=0.99 was found between the percentage of Substance P hydrolysis and the incubation time at 25° C. Ten 1M Phosphoramidon or 10 µM Thiorphan exhibits relatively the same inhibitory activity (60-65% inhibition). The QHNPR (SEQ ID NO: 1) peptide (10 µM) is found to be an efficient inhibitor: 75% inhibition of Substance P degradation when it is alone, more than 90% when it is combined with GEMBA (10 µM) and DPPIV inhibitor (10 µM). These latter, however, appear to exhibit an inherent inhibiting activity of Substance P degradation by fresh spinal tissue.

Otherwise, in this experiment, the effect of inhibitors is proportionally stable as a function of the duration of incubation over the 30 min. incubation period (r=0.99).

Determination of the $IC_{50}$

The dose-response curve of the SMR1-QHNPR (SEQ ID NO: 1) inhibitory effect on 3H-Substance P degradation by spinal cord membrane preparations, shown in FIG. 3-B right panel, allows the calculation of an $IC_{50}$ value (concentration of the inhibitor reducing by half the degradation of 3H-substance P) of about $1.10^{-7}$ M. In the same experiment, comparison with Phosphoramidon reveals that protection of the exogenous Substance P by SMR1-QHNPR (SEO ID NO: 1) is still equivalent to that obtained with Phosphoramidon (FIG. 3-B left panel). Furthermore, the QHNPR (SEQ ID NO: 1) peptide combined with the inhibitors of CPB and DPPIV exhibits a very high NEP inhibiting activity, greater than that of phosphoramidon (FIG. 3-B, left panel).

2.2.3. Record

The metabolism rate of the NEP-sensitive peptides has been measured using tritiated substrate coupled to chromatographic analysis (Substance P) or using native substrate coupled to specific RIA quantification (Met-enkephalin). Under conditions of initial velocity measurement of the NEP enzymatic activity, an almost complete inhibition of exogenous Met-enkephalin or Substance P catabolism resulting from addition of SMR1-Pentapeptide has been observed: the concentration of SMR1-QHNPR (SEQ ID NO: 1) which reduces by half the degradation of Substance P by spinal cord tissues, was calculated to be $1.10^{-7}$M and its inhibitory potency is equivalent to that of two well-known NEP-specific inhibitors, Thiorphan and Phosphoramidon. From these results it appears that, ex vivo, the SMR1-Pentapeptide efficiently prevents the spinal NEP-induced degradation of both neuropeptides involved in the control of spinal pain perception, e.g. Substance P and Met-Enkephalin.

Example 2

Anti-Depressive Effect of SMR1-QHNPR Peptide in the Behavioral Despair Test

Forty male Wistar/AF EOPS rats (Iffa-Credo Breeding Centre, 69-St-Germain sur l'Arbresle, France), weighing 300 to 320 g, were used. On arrival, the rats were labelled and distributed randomly in pairs into type F polycarbonate cages (48×27×20 cm, U.A.R., 91-Epinay-Sur-Orge, France). The animals were stabled in an air-conditioned animal house, at a temperature of 22-24° C. The rats were given food (M25 croquettes, Ets Pietrement, 77-Provins, France) and drink ad libitum and were subjected to a 12-hour light-darkness cycle.

After one week of familiarization with the laboratory conditions, the rats were weighed and distributed randomly into 3 treatment groups (n=12). The rats of the different groups will all be handled in the same way and under the same conditions.

The behavioral despair test takes place over two sessions:

a 15-minute test session;

a 5-minute retest session, performed 24 hours later.

During the test session, the rat was subjected to forced swimming in a Plexiglas cylinder (20 cm in diameter and 50 cm in height, containing 25 cm of water at 25° C.) and its behavior was recorded over 15 minutes. At the end of the test, the rat was removed from the water, dried gently, treated and then returned to its dwelling cage.

During the retest, 24 hours later, the rat was again placed in the water and its behavior was recorded over 5 minutes.

The recorded variables are the period of immobility during the first 5 minutes of both the test and the retest.

The peptide FG-005 (SMR1-QHNPR) (SEQ ID NO: 1) was suspended at a rate of 500 µg per 5 ml of 0.01N acetic acid, and then diluted with PBS to be administered at doses of 50 and 100 µg/kg via the i.v. route into the dorsal caudal vein of the rat, immediately after the test and 300 and 5 minutes before the retest the following day.

| Group | Rat per group | Treatment | Dose (µg/kg) | Volume (ml/kg) | Administrations before the retest (minutes) |
|---|---|---|---|---|---|
| Vehicle | 10 | Acetic acid + PBS | — | 0.7 | 1440, 300, 5 |
| FG 50 | 10 | FG-005 | 50 | 0.7 | 1440, 300, 5 |
| FG 100 | 10 | FG-005 | 100 | 0.7 | 1440, 300, 5 |
| 8-OH-DPAT | 10 | 8-OH-DPAT | 500 | 1 | 1440, 300, 30 |

ANOVA in factorial measurements was used to demonstrate the existence of heterogeneity among the groups. A bilateral probability paired t test was used to compare the two periods of immobility of the test with those of the retest in each of the groups. The results are expressed as an average ±standard error of mean (SEM)(FIG. 4). The statistical and graphical processing was performed using Statview5 and DeltaGraph® Pro 3.5 software.

The analysis of variance [F(3.36)=1.57; N.S.] shows no heterogeneity of the periods of immobility for the different groups during the test 1 before any treatment and reveals a heterogeneity among these periods of immobility after treatment [F(3.36)=13.12; p<0.001].

The bilateral probability paired t test shows that the control rats significantly increase their period of immobility during the retest compared with the test. Conversely, the rats treated with 8-OH-DPAT significantly reduce their period of immobility during the retest compared with the test.

The immobility time of the rats treated with FG-005 at a dose of 50 µg/kg increase their period of immobility during the retest and those treated at a dose of 100 mg/kg reduce it. However, in both cases, the differences are not statistically significant (NS).

TABLE

Immobility periods during the test and retest sessions (mean ± SD)

|  | Vehicle i.v. (n = 10) | FG-50 50 µg/kg, i.v. (n = 10) | FG-100 100 µg/kg, i.v. (n = 10) | 8-OH-DPAT 0.5 mg/kg, i.p. (n = 10) |
|---|---|---|---|---|
| Test | 104.80 ± 11.08 | 119.00 ± 13.79 | 138.30 ± 11.03 | 109.20 ± 11.43 |
| Retest | 187.80 ± 20.41 | 141.20 ± 21.28 | 121.50 ± 17.47 | 31.60 ± 11.51 |
| Paired t test (bilat. prob.) (Test vs. Retest) | t = 4.14; p < 0.005 | t = 1.50; N.S. | t = 1.20; N.S. | t = 10.91; p < 0.001 |

Under our experimental conditions, the period of immobility of the control rats is significantly longer during the retest compared with the test. This clearly shows the resignation of the rats, which no longer seek to escape the rainy aquatic environment.

The rats treated with the peptide FG-005, at doses of 50 and 100 µg/kg, i.v., immediately after the depression test and 300 and 5 minutes before the retest the following day, do not increase their periods of immobility during the retest. The rats of the two groups show equivalent swimming activity during the two sessions. Since the rats showed no behavioral resignation, the peptide FG-005 is thought to have an antidepressant effect in rats. 8-OH-DPAT, used as reference substance, showed significant anti-resignation effect.

The invention claimed is:

1. A method of treating a mood disorder, the method comprising:
  administering to a subject in need thereof an amount effective to treat said mood disorder of at least one submandibular rat 1 protein (SMR1) peptide or modified SMR1 peptide that modulates the interaction between a mature peptide QHNPR (SEQ ID NO: 1) generated from the SMR1 and a metallopeptidase,
  wherein the SMR1 peptide comprises the peptide of SEQ ID NO: 1 and the modified SMR1 peptide comprises the sequence QHNPR (SEQ ID NO: 1) in which at least one L-amino acid has been replaced by a D-amino acid, and/or has been modified by at least one of the following:
  adding a protecting group to one or more amino acid side chains,
  adding a protecting group to NH2 or COOH groups,
  replacing one or more amine bonds with a non-amide bond,
  introducing one or more double bonds,
  introducing retroinversion or reduction isomers of the CO—NH amide bonds,
  methylating at least one amide,
  and conducting cyclization.

2. The method of claim 1 in which the SMR1 peptide is administered.

3. The method of claim 1 in which the modified SMR1 peptide is administered which has at least one L-amino acid replaced by a D-amino acid.

4. The method of claim 1 in which the modified SMR1 peptide is administered which has been modified by at least one of the following:
  adding a protecting group to one or more amino acid side chains,
  adding a protecting group to NH2 or COOH groups,
  replacing one or more amide bonds with a non-amide bond,
  introducing one or more double bonds,
  introducing retroinversion or reduction isomers of the CO—NH amide bonds,
  methylating at least one amide,
  and conducting cyclization.

5. The method of claim 1, wherein said mood disorder is depression.

* * * * *

UNITED STATES PATENT AND TRADEMARK OFFICE
CERTIFICATE OF CORRECTION

PATENT NO. : 7,423,020 B2 Page 1 of 1
APPLICATION NO. : 10/451073
DATED : September 9, 2008
INVENTOR(S) : Rougeot et al.

It is certified that error appears in the above-identified patent and that said Letters Patent is hereby corrected as shown below:

On the title page, Item (30), the Foreign Application Priority Data is incorrect. Item (30) should read:

-- (30)     Foreign Application Priority Data

Dec. 22, 2000     (EP) ………………….. 00403670 --

Signed and Sealed this

Fourth Day of August, 2009

JOHN DOLL
*Acting Director of the United States Patent and Trademark Office*